United States Patent [19]

Nardi et al.

[11] Patent Number: 4,510,140
[45] Date of Patent: Apr. 9, 1985

[54] THERAPEUTICALLY EFFECTIVE ω-(4-(2-PYRIDYL)-PIPERAZINO)-ALKANOYLANILIDES

[75] Inventors: Dante Nardi; Alberto Catto; Alberto Tajana; Pietro Cazzulani; Gabriele Graziani, all of Milan, Italy

[73] Assignee: Recordati S.A., Chiasso, Switzerland

[21] Appl. No.: 412,818

[22] Filed: Aug. 30, 1982

[30] Foreign Application Priority Data

Sep. 3, 1981 [GB] United Kingdom ............... 8126754

[51] Int. Cl.³ ............... C07D 241/04; A61K 31/495
[52] U.S. Cl. ............................................... 544/360
[58] Field of Search ..................... 544/360; 424/250

[56] References Cited

FOREIGN PATENT DOCUMENTS 530723 9/1956 Canada ............................. 544/360
1279843 6/1972 United Kingdom ............... 544/360

Primary Examiner—Donald G. Daus
Assistant Examiner—S. A. Gibson
Attorney, Agent, or Firm—Burns, Doane, Swecker & Mathis

[57] ABSTRACT

The ω-[4-(2-pyridyl)-piperazino]-alkanoylanilide compounds having the structural formula (I):

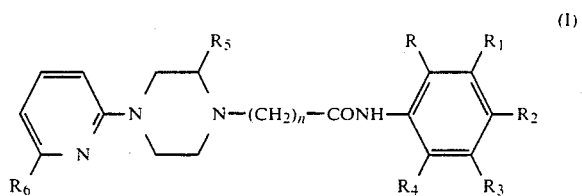

wherein n is 1, 2 or 3, each of R, $R_1$, $R_2$ $R_3$, and $R_4$ is independently hydrogen, halogen, alkyl, alkoxy, OH, $NH_2$, $CF_3$, CN, alkylthio, 1-hydroxyalkyl, alkanoyl, $NH_2CO$, $NH_2SO_2$, alkoxycarbonyl, alkylsulfonyl, benzyloxy, alkanoylamino, $NH_2CONH$, 3-phenylureido, 3-alkylureido or alkoxyoxalylamino, $R_5$ is hydrogen or alkyl, and $R_6$ is hydrogen or alkoxy, and the pharmaceutically acceptable salts thereof, are effective antianaphylactics, antibronchospastics, antihistaminics, sedatives, analgesics, antiserotonics and blood-pressure-lowering agents.

19 Claims, No Drawings

THERAPEUTICALLY EFFECTIVE ω-(4-(2-PYRIDYL)-PIPERAZINO)-ALKANOYLANILIDES

FIELD AND SUMMARY OF THE INVENTION

The present invention relates to novel ω-[4-(2-pyridyl)-piperazino]-alkanoylanilide compounds, to the pharmaceutically acceptable salts thereof, to processes for the preparation thereof and to a variety of pharmaceutical compositions comprising same.

The novel ω-[4-(2-pyridyl)-piperazino]-alkanoylanilide compounds according to this invention have the structural formula (I):

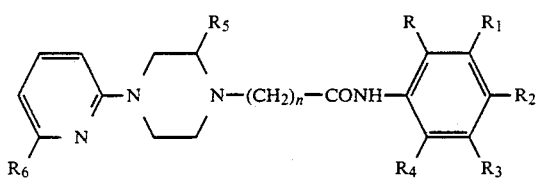

wherein n is 1, 2 or 3, each of R, $R_1$, $R_2$, $R_3$ and $R_4$ is independently hydrogen, halogen, alkyl, alkoxy, hydroxy, nitro, amino, trifluoromethyl, cyano, alkylthio, 1-hydroxyalkyl, alkanoyl, carbamoyl, sulfamoyl, alkoxycarbonyl, alkylsulfonyl, benzyloxy, alkanoylamino, ureido, 3-phenylureido, 3-alkylureido or alkoxyoxalylamino, $R_5$ is hydrogen or alkyl, and $R_6$ is hydrogen or alkoxy, and the pharmaceutically acceptable acid addition salts of such ω-[4-(2-pyridyl)-piperazino]-alkanoylanilide compounds. By the terms "alkyl" and "alkoxy" as used above, whether alone or in combination, there are intended such groups having from 1 to 4 carbon atoms; by the term "alkanoyl" as used above, whether alone or in combination, there is intended a group having from 2 to 4 carbon atoms.

DETAILED DESCRIPTION OF THE INVENTION

More particularly according to this invention, the compounds having the structural formula (I) wherein n, $R_5$ and $R_6$ are as above-defined, and each of R, $R_1$, $R_2$, $R_3$ and $R_4$ is independently hydrogen, halogen, alkyl, alkoxy, hydroxy, nitro, trifluoromethyl, cyano, alkylthio, 1-hydroxyalkyl, alkanoyl, carbamoyl, sulfamoyl, alkoxycarbonyl, alkylsulfonyl or benzyloxy, are facilely prepared by reacting a 4-(2-pyridyl)-piperazine having the structural formula (II):

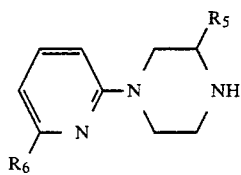

wherein $R_5$ and $R_6$ are as above-defined, with an ω-haloalkanoylanilide having the structural formula (III):

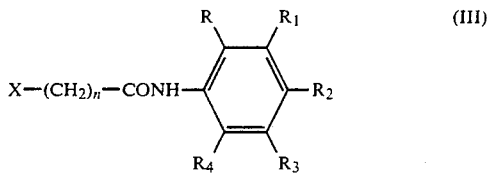

wherein X represents a halogen atom, n is as above-defined and R, $R_1$, $R_2$, $R_3$ and $R_4$ are each as defined in this sentence. The reaction is preferably carried out in the presence of an organic or inorganic base, such as triethylamine or alkali metal bicarbonate, and a solvent, such as an alkanol or a ketone having up to 4 carbon atoms, at the reflux temperature of the solvent.

Those compounds having the structural formula (I) wherein n is 2, $R_5$ and $R_6$ are as defined above and R, $R_1$, $R_2$, $R_3$ and $R_4$ are as defined in the preceding paragraph are alternatively conveniently prepared by reacting a 4-(2-pyridyl)-piperazine having the above structural formula (II) with an acryloylanilide having the structural formula (IV):

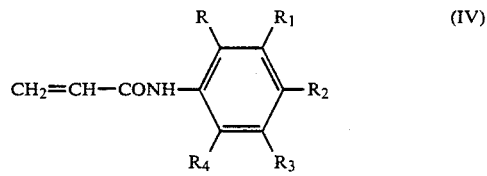

wherein R, $R_1$, $R_2$, $R_3$ and $R_4$ are as defined in the preceding paragraph. This particular reaction is preferably carried out in a solvent, such as dimethylsulfoxide, chloroform or an aromatic hydrocarbon, for example, toluene or xylene.

The compounds having the structural formula (I) wherein any of R, $R_1$, $R_2$, $R_3$ and $R_4$ is an amino group are readily prepared by reduction of the corresponding nitro derivative, prepared by one of the aforementioned processes, the reduction being effected with hydrogen in the presence of a palladium-on-carbon catalyst and a solvent. These amino derivatives are themselves starting materials for the preparation of the corresponding compounds having the structural formula (I) wherein any or R, $R_1$, $R_2$, $R_3$ and $R_4$ is ureido, 3-phenylureido, 3-alkylureido, alkanoylamino or alkoxyoxalylamino, by reaction with an alkali metal, phenyl or alkyl isocyanate, alkanoic acid anhydride or alkoxyoxalyl halide, respectively. Such reaction is advantageously carried out at room temperature or under heating for a period of from 12 to 36 hours, and the product is then isolated by conventional separation, drying and crystallization techniques. If an alkoxyoxalyl halide used, the reaction should be carried out in the presence of a base, preferably triethylamine, to bind the hydrogen halide formed.

All of the processes described above are within the ambit of this invention.

The pharmaceutically acceptable salts according to the invention are prepared from the free bases thereof in conventional manner. Preferred pharmaceutically acceptable acid addition salts are those of hydrochloric, sulfuric, nitric, phosphoric, acetic, propionic, succinic, maleic, citric, tartaric, benzoic, methanesulfonic and toluenesulfonic acids.

The subject novel ω-[4-(2-pyridyl)-piperazino]-alkanoylanilides and the pharmaceutically acceptable salts thereof according to the invention possess valuable pharmacological properties, i.e., antianaphylactic, antibronchospastic, antihistaminic, sedative, analgesic, antiserotonic and blood-pressure-lowering properties or effects.

Accordingly, the present invention also features pharmaceutical compositions comprising a pharmaceutically effective amount of a compound having the structural formula (I) as above-defined, or a pharmaceutically acceptable salt thereof, in admixture with conventional pharmaceutically acceptable dileunt or carrier. Suitable such carriers and unit dosage amounts will be apparent to those skilled in this art. Compare, for example, *Remington's Pharmaceutical Sciences*, 4th Edition (1970). The $LD_{50}$ of the alkanoylanilides according to the invention was determined in the mouse, both in C. S. Weil, following the method described *Biometrics*, 8, 249 (1952). The results obtained were as follows, with the designating for the active compounds corresponding to those set forth in the following specific examples:

TABLE 1

| Active compound | $LD_{50}$ in Mg/Kg | |
|---|---|---|
| | ip | os |
| 1 | 0.90 | — |
| 2 | 0.65 | — |
| 3 | 0.71 | 1.16 |
| 4 | 0.42 | 2.07 |
| 5 | 0.91 | 1.21 |
| 6 | 0.47 | 0.81 |
| 7 | 1.11 | 1.29 |
| 8 | >2.25 | >6.7 |
| 11 | 1.05 | 1.53 |
| 12 | >2.35 | >7.05 |
| 13 | 0.48 | 1.5 |
| 14 | 3.25 | 5.97 |
| 15 | 0.57 | — |
| 16 | 1.16 | 1.35 |
| 17 | 1.01 | 1.58 |
| 18 | 0.80 | — |
| 19 | 0.69 | 0.92 |
| 20 | >2.5 | 5.2 |
| 21 | 2.38 | 3.74 |
| 22 | 3.2 | 2.08 |
| 23 | 0.9 | 0.85 |
| 24 | 1.18 | 2.97 |
| 25 | 0.53 | 1.60 |
| 27 | — | >6.81 |
| 28 | >2.15 | >6.5 |
| 29 | 2.08 | 3.7 |
| 30 | 0.42 | 1.2 |
| 31 | — | 4.39 |
| 32 | — | 1.57 |
| 33 | 1.29 | 2.64 |
| 34 | — | >7.1 |
| 35 | 0.62 | 0.96 |
| 36 | 0.8 | 1.24 |
| 37 | 0.56 | 1.17 |
| 38 | 0.37 | 0.67 |
| 39 | 2.30 | >6.91 |
| 40 | 0.68 | 1.11 |
| 41 | 0.66 | 0.92 |
| 42 | — | >8.4 |
| 43 | 0.39 | 0.62 |

In order to evaluate the antianaphylactic activity of the subject novel compounds, the method of Goose and Blair was followed, in which passive cutaneous anaphylaxis was induced in the rat with homologous antibodies [*Immunology*, 16, 749 (1969)]. Female albino rats were immunized intramuscularly with egg albumin and intraperitoneally with Hemophylus pertussis vaccine.

Twelve days after treatment, the animals were bled and the sera thus obtained were injected intradermally into another group of rats. Twenty-four hours later, the animals were challenged with an i.v. solution of ovoalbumin and Evans blue dye, and sacrificed after 30 minutes. The test drugs were administered by different routes of administration and at different times before the challenge. Inhibition of spot areas ($ED_{50}$) was determined.

The obtained data are reported in the following Table II:

TABLE II

| Active compound | PCA Test - $ED_{50}$ in mM/Kg | |
|---|---|---|
| | ip | os |
| 1 | 0.337 | — |
| 2 | 0.212 | — |
| 3 | 0.019 | |
| 4 | 0.056 | 0.068 |
| 5 | 0.089 | — |
| 6 | 0.027 | — |
| 7 | 0.027 | 0.074 |
| 9 | — | — |
| 10 | — | — |
| 11 | 0.16 | — |
| 12 | 0.13 | 0.18 |
| 13 | 0.104 | — |
| 14 | 0.032 | 0.106 |
| 15 | 0.019 | 0.026 |
| 16 | 0.064 | 0.061 |
| 17 | | 0.067 |
| 18 | 0.081 | 0.013 |
| 19 | — | 0.054 |
| 20 | 0.12 | 0.17 |
| 21 | 0.27 | 0.16 |
| 22 | — | 0.1 |
| 23 | — | 0.17 |
| 24 | — | 0.039 |
| 25 | 0.11 | 0.055 |
| 27 | 0.12 | 0.092 |
| 28 | — | 0.073 |
| 30 | — | 0.23 |
| 31 | — | 0.13 |
| 33 | 0.151 | 0.047 |
| 35 | | 0.039 |
| 36 | — | 0.029 |
| 38 | — | 0.044 |
| 39 | | 0.073 |
| 40 | — | 0.073 |
| 41 | 0.22 | 0.028 |

The antibronchospastic activity was determined according to the method of Konzett and Rössler [*Arch. exp. Path. Pharmakol.*, 195, 71 (1940)], determining the inhibition of bronchospasm induced in anaesthetized guinea-pig by histamine. For this purpose, the bronchospasms were induced by administering intravenously to the animals 0.5–2.5 μg/Kg of hystamine. Inhibition ($ED_{75}$) was determined one minute after the injection of the drug under test, and the results obtained are reported in the following Table III:

TABLE III

| Active compound | $ED_{75}$ μM/Kg i.v. |
|---|---|
| | Obtained values |
| 3 | 0.24 |
| 4 | 0.37 |
| 5 | 3.89 |
| 6 | 0.94 |
| 7 | 0.02 |
| 11 | 0.23 |
| 12 | 0.23 |
| 13 | 0.02 |
| 14 | 0.48 |
| 15 | 1.56 |
| 16 | 1.93 |
| 17 | 0.47 |
| 18 | 1.57 |
| 19 | 0.14 |
| 20 | 0.49 |

TABLE III-continued

| Active compound | ED$_{75}$ μM/Kg i.v. Obtained values |
|---|---|
| 21 | 1.1 |
| 22 | 1.63 |
| 23 | 0.61 |
| 24 | 0.59 |
| 25 | 0.4 |
| 27 | 0.97 |
| 28 | 0.29 |
| 29 | 0.58 |
| 30 | 1.75 |
| 32 | 2.4 |
| 33 | 1.12 |
| 35 | 2.27 |
| 36 | 0.4 |
| 39 | 0.89 |
| 40 | 0.2 |
| 41 | 0.17 |

In order to further illustrate the present invention and the advantages thereof, the following specific examples are given, it being understood that same are intended only as illustrative and in nowise limitative.

EXAMPLE 1

Preparation of
2,6-Dimethyl-α-[4-(2-pyridyl)-piperazino]-acetanilide;
(I:R=R$_4$=CH$_3$, R$_1$=R$_2$=R$_3$=R$_5$=R$_6$=H, n=1);
Active compound 1

4.2 g of sodium bicarbonate and 9.88 g of 2,6-dimethyl-α-chloro-acetanilide dissolved in 100 ml of acetone were added to 8.16 g of 1-(2-pyridyl)-piperazine dissolved in 25 ml of acetone. The mixture was refluxed under stirring for 5 hours. Upon completion of the reaction, the precipitate was filtered off, collected and washed with acetone. Active compound 1 was dried and crystallized from ethyl acetate. Yield 8.8 g, mp 144°–145° C.

The free base, dissolved in isopropanol, was treated with hydrogen chloride in isopropanol to provide the corresponding hydrochloride, mp 189°–191° C.

EXAMPLE 2

Preparation of
2,3,5,6-Tetramethyl-α-[4-(2-pyridyl)-piperazino]-acetanilide; (I:R=R$_1$=R$_3$=R$_4$=CH$_3$,
R$_2$=R$_5$=R$_6$=H, n=1); Active compound 2

To a mixture consisting of 1.63 g of 1-(2-pyridyl)-piperazine and 0.84 g of sodium bicarbonate in 5 ml of isopropanol, a suspension of 2.47 g of 2,3,5,6-tetramethyl-α-chloroacetanilide in 30 ml of isopropanol was added at room temperature. The entire reaction mass was stirred and refluxed for 5 hours. Upon completion of the reaction, the crude product was filtered off, the solvent evaporated and the residue washed with boiling water, dried, and crystallized from ethyl acetate (or isopropanol). Yield 1.8 g, mp 151°–152° C. The hydrochloride, obtained in conventional manner, melted at 265°–267° C.

EXAMPLE 3

Preparation of
4-Methoxy-α-[4-(2-pyridyl)-piperazino]-propionylanilide; (I:R=R$_1$=R$_3$=R$_4$=R$_5$=R$_6$=H, R$_2$=CH$_3$O, n=2); Active compound 3

To 3.19 g of 4-methoxy-acryloylanilide dissolved in 18 ml of benzene, 2.93 g of 1-(2-pyridyl)-piperazine dissolved in 9 ml of benzene were added. The mixture was refluxed for 3 hours. Upon completion of the reaction, the mixture was cooled, the precipitate filtered off and crystallized from ethanol. Yield 4.52 g, mp 127°–128° C. The corresponding hydrochloride, crystallized from 95% ethanol as hemihydrate, melted at 207°–211° C.

EXAMPLE 4

Preparation of
3-Nitro-β-[4-(2-pyridyl)-piperazino]-propionylanilide;
(I:R=R$_2$=R$_3$=R$_4$=R$_5$=R$_6$=H, R$_1$=NO$_2$, n=2);
Active compound 4

13.45 g of 3-nitro-acryloylanilide (obtained from 3-nitroaniline and acrylic acid chloride) and 11.41 g of 1-(2-pyridyl)-piperazine in 140 ml of toluene were refluxed under stirring for 16 hours. Upon completion of the reaction, the mixture was cooled and the precipitate thus formed was filtered off and crystallized from toluene. Yield 22.19 g, mp 133°–134° C. The hydrochloride, crystallized from 90% ethanol, melted at 228°–230° C. Starting from 4-nitro-acryloylanilide instead of 3-nitro-acryloylanilide, there was obtained active compound 6, 4-nitro-β-[4-(2-pyridyl)-piperazino]-propionylanilide; (I:R=R$_1$=R$_3$=R$_4$=R$_5$=R$_6$=H, R$_2$=NO$_2$, n=2); mp 157°–158° C.

EXAMPLE 5

Preparation of
2-Benzyloxy-5-acetyl-β-[4-(2-pyridyl)-piperazino]-propionylanilide; (I:R=R$_2$=R$_3$=R$_5$=R$_6$=H,
R$_1$=COCH$_3$, R$_4$=C$_6$H$_5$CH$_2$0, n=2); Active compound 5

A mixture comprising 14.75 g of 3-acryloylamino-4-benzyloxy-acetophenone and 8.1 g of 1-(2-pyridyl)-piperazine in 150 ml of dichloromethane was refluxed for 1 hour, and then allowed to stand for one day at room temperature. The solvent was evaporated off and the crude product thus formed purified on a silica gel column using ethyl acetate as eluent. Active compound 5 was cyrstallized from 60% ethanol or ligroin, mp 134°–135° C. Yield 14.5 g.

EXAMPLE 6

Preparation of
4-Amino-β-[4-(2-pyridyl)-piperazino]-propionylanide;
(I:R=R$_1$=R$_3$=R$_4$=R$_5$=R$_6$=H,R$_2$=NH$_2$,n=2);
Active compound 7

To 8.88 g of 4-nitro-β-[4-(2-pyridyl)-piperazino]-propionylanilide, obtained as described in Example 4, dissolved in 350 ml of methanol, 0.5 g of 10% palladium-on-carbon were added. The entire reaction mass was hydrogenated at the initial pressure of 601 lbs. After 8 hours the catalyst was collected on a filter and the methanol evaporated off. The residue was dissolved in chloroform and chromatographed on a silica gel column using a chloroform:methanol mixture (98:2 by volume) as eluent. The product was crystallized from ethyl acetate, yield 5.97 g, mp 103°–104° C.

EXAMPLE 7

Preparation of
4-(3-Phenylureido)-β-[4-(2-pyridyl)-piperazino]-propionylanide;
(I:R=R$_1$=R$_3$=R$_4$=R$_5$=R$_6$=H,R$_2$=C$_6$H$_5$NH-CONH,n=2); Active compound 8

6.5 g of active compound 7, obtained as described in Example 6, and 2.38 go of phenylisocyanate in 60 ml of toluene, were stirred at 20°–25° C. for 8 hours. After being permitted to stand for one night at room temperature, the solvent was evaporated off under vacuum, and the residue was crystallized from dioxane:water (5:1 by volume) to provide 6.09 g of the compound 8; Mp>260° C.

EXAMPLE 8

Preparation of
4-Sulfamoyl-β-[4-(2-pyridyl)-piperazino]-propionylanilide;
(I=R=R$_1$=R$_3$=R$_4$=R$_5$=R$_6$=H,R$_2$=NH$_2$SO$_2$,n=2); Active compound 9

6.78 g of 4-sulfamoylacryloylanilide and 5.38 g of 1-(2-pyridyl)-piperazine dissolved in 15 ml of DMSO, were heated at 50° C. for 16 hours under stirring. Upon completion of the reaction, the mixture was poured into water and the product thus formed was collected, filtered off, dried, and crystallized from methanol. Yield 9 g, mp 207°–211° C.

EXAMPLE 9

Preparation of
4-Ureido-β-[4](2-pyridyl)-piperazino]-propionylanilide;
(I:R=R$_1$=R$_3$=R$_4$=R$_5$=R$_6$=H,R$_2$=NH$_2$CONH, n=2); Active compound 10

To 3.25 g of active compound 7, obtained as described in Example 6, dissolved in 50 ml of 1N hydrochloric acid, 1.64 g of potassium isocyanate were added. The entire reaction mass was stirred at 20° to 25° C. for 8 hours. After one night at room temperature, the mixture was cooled on ice and a saturated solution of sodium carbonate added thereto. The precipitate thus formed was filtered off, washed with hot acetone, filtered again and crystallized from methanol. Mp 250° C. (with decomposition), yield 2.2 g.

EXAMPLE 10

Preparation of
4-Propionamide-β-[4-(2-pyridyl)-piperazino]-propionylanilide;
(I:R=R$_1$R$_3$=R$_4$=R$_5$=R$_6$=H,R$_2$=C$_2$H$_5$CONH,n=2); Active compound 11

To 8.13 g of active compound 7, obtained as described in Example 6, in 35 ml of chloroform, 3.64 g of propionic anhydride were added. The mixture was refluxed under stirring for 8 hours. Upon completion of the reaction, the solvent was evaporated off under vacuum and the residue was treated with sodium bicarbonate. The product was filtered, dried, and cyrstallized from ethanol.

Yield 7.22 g, mp 195°–197° C. The corresponding hydrochloride obtained as hydrate, melted at 190°–192° C.

EXAMPLE 11

Preparation of
4-Ethoxyoxyalylamido-β-[4-(2-pyridyl)-piperazino]-propionylanilide;
(I:R=R$_1$=R$_3$=R$_4$=R$_5$=R$_6$=H,R$_2$=C$_2$H$_5$OOC.CONH, n=2); Active compound 12

To 8.13 g of active compound 7, obtained as described in Example 6, dissolved in 50 ml of chloroform, 4.2 ml of triethylamine and 3.35 ml of ethyl chloroxalate were added under stirring. The temperature was maintained at 7° C. during the addition. After one night at room temperature, insoluble substances were removed from the solution, the solvent was evaporated off and the residue was suspended in water, filtered and crystalized from ethanol. Yield 6.5 g, mp 157°–158° C.

EXAMPLE 12

Preparation of
4-Acetyl-β-[4-(2-pyridyl)-piperazinyl]-propionylanilide;
(I:R=R$_1$=R$_3$=R$_4$=R$_5$=R$_6$=H,R$_2$=CH$_3$CO,n=2); Active compound 13

A mixture comprising 9.4 g of 4-acryloylaminoacetophenone and 8.1 g of 1-(2-pyridyl)-piperazine in 200 ml of benzene was maintained for 1 to 2 days at 20° to 25° C. under stirring. Upon completion of the reaction, the solvent was evaporated off and the residue chromatographed on a silica gel column using ethyl acetate:methanol (7:3 by volume) as eluent.

The crude product, after evaporation of the solvents, was crystallized from 40% ethanol to provide 10 g of active compound 13, melting at 134°–136° C. The corresponding hydrochloride, isolated as hemihydrate, melted at 235°–240° C.

EXAMPLE 13

Preparation of
4-(1-Hydroxyethyl)-β-[4-(2-pyridyl)-piperazinyl]-propionylanilide;
(I:R=R$_1$=R$_3$=R$_4$=R$_5$=R$_6$=H,R$_2$=CH$_3$CH(OH),n=2); Active compound 14

To 14.8 g of active compound 13, obtained as described in Example 12, in 280 ml of ethanol, 1.52 g of sodium borohydride were added. The solution was maintained at 20° to 25° C. for 27 hours. Upon completion of the reaction, the precipitate thus formed was separated off and suspended in water, and dilute hydrochloric acid was added until the pH reached 6. The mixture was then treated with sodium bicarbonate until the pH reached 8 and then the product was extracted with 500 ml of chloroform. The organic phase was separated off and provided a product cyrstallizing from ethanol. Yield 9.5 g, mp 157°–161° C.

EXAMPLE 14

Following the procedures outlined in the foregoing Examples 1 to 13, the compounds listed herein below in Table IV were prepared:

TABLE IV

| ACTIVE COMPOUND | n | R | R$_1$ | R$_2$ | R$_3$ | R$_4$ | R$_5$ | R$_6$ | Mp °C.* |
|---|---|---|---|---|---|---|---|---|---|
| 15 | 2 | Me | Me | H | | Me | Me | H | H | 178-8 (176-81) |

TABLE IV-continued

| ACTIVE COMPOUND | n | R | $R_1$ | $R_2$ | $R_3$ | $R_4$ | $R_5$ | $R_6$ | Mp °C.* |
|---|---|---|---|---|---|---|---|---|---|
| 16 | 2 | H | H | H | H | H | H | H | 79–81 |
| 17 | 2 | Me | H | H | H | H | H | H | 99–102 (201–2) |
| 18 | 2 | Me | H | H | H | Me | H | H | 121-2 (134) |
| 19 | 2 | H | H | OEt | H | H | H | H | 129–30 (228–9) |
| 20 | 2 | H | H | OH | H | H | H | H | 189–90 (228–30) |
| 21 | 2 | H | $NO_2$ | OH | H | H | H | H | 148–9 |
| 22 | 2 | $NH_2$ | H | H | H | H | H | H | 149–50 |
| 23 | 2 | H | $NH_2$ | H | H | H | H | H | 148–50 (230–1) |
| 24 | 2 | H | H | $NH_2$ | H | H | Me | H | 268–70 |
| 25 | 2 | H | H | $NH_2$ | H | H | H | OMe | 96–8 (207) |
| 26 | 2 | $NH_2$ | H | $NH_2$ | H | H | H | H | 155–6 |
| 27 | 2 | H | H | NHCOMe | H | H | H | H | 187–8 |
| 28 | 2 | H | H | NHCONHMe | H | H | H | H | 213–4 (209–12) |
| 29 | 2 | $NO_2$ | H | H | H | H | H | H | 90–2 (220–2) |
| 30 | 2 | H | H | $NO_2$ | H | H | Me | H | 129–30 (210–2) |
| 31 | 2 | H | H | $NO_2$ | H | H | H | OMe | 126–8 (207–11) |
| 32 | 2 | H | $NO_2$ | H | $NO_2$ | H | H | H | 186–7 |
| 33 | 2 | Cl | H | H | H | H | H | H | 95–6 (181–5) |
| 34 | 2 | $NO_2$ | H | H | H | H | H | OMe | 103–4 (212–3) |
| 35 | 2 | H | H | Cl | H | H | H | H | 118–9 (202–3) |
| 36 | 2 | Cl | H | H | H | Cl | H | H | 155–7 (270–2) |
| 37 | 2 | H | $CF_3$ | H | H | H | H | H | 100–2 (203–4) |
| 38 | 2 | $NH_2$ | H | H | H | H | H | OMe | 148–50 (179 dec) |
| 39 | 2 | COMe | H | H | H | H | H | H | 90–1 (230–2) |
| 40 | 2 | H | COMe | H | H | H | H | H | 109–11 (223–5) |
| 41 | 2 | H | H | COOEt | H | H | H | H | 92–5 (227–9) |
| 42 | 2 | H | H | SMe | H | H | H | H | 128–9 |
| 43 | 2 | H | H | CN | H | H | H | H | 112–4 (247–8) |
| 44 | 2 | H | H | $CONH_2$ | H | H | H | H | 227–8 |
| 45 | 2 | H | OMe | H | H | H | H | H | 102–3 |

*When two melting points are reported, the second one refers to a pharmaceutically acceptable salt; unless otherwise indicated, the hydrochloride is intended.

EXAMPLE 15

Preparation of 3,6-Dimethyl-4-nitro-β-[4-(2-pyridyl)-piperazino]-propionylanilide; (I:R—$R_3$=$R_5$=$R_6$=H,$R_1$=$R_4$=$CH_3$, $R_2$=$NO_2$,n=2); Active compound 46

Following the procedures of Example 4, but starting from 3,6-dimethyl-4-nitro-acryloylanilide instead of 3-nitro-acryloylanilide, the active compound 46, melting at 176°–177° C., was obtained.

This compound was transformed into its dihydrochloride which melted at 262°–266° C. Using 10% palladium-on-carbon and hydrogenating, the corresponding 3,6-dimethyl-4-amino derivative was obtained, isolated as its trihydrochloride hydrate, mp 266°–171° C. (I: n=2, R=$R_3$=$R_5$=$R_6$=H, $R_1$=$R_4$=$CH_3$, $R_2$=$NH_2$); Active compound 47. In the same manner, but starting from tetramethyl-4-nitro-acryloylanilide, 2,3,5,6-tetramethyl-4-nitro-β-[4-(2-pyridyl)-piperazino]-propionylanilide was obtained, melting at 166°–167° C. (the dihydrochloride melted at 273°–275° C.). From this compound, as described above, the corresponding amino derivative was prepared, mp 170°–172° C. These compounds have the structural formula (I) in which n=2, $R_5$=$R_6$=H, R=$R_1$=$R_3$=$R_4$=$CH_3$, $R_2$=$NO_2$ or $NH_2$, and are active compounds 48 and 49 respectively.

EXAMPLE 16

Preparation of 4-Sulfamoyl-β-[4-(2-pyridyl)-piperazino]-butyrylanilide; (I:R=$R_1$=$R_3$=$R_4$=$R_5$=$R_6$=H, $R_2$=$SO_2NH_2$, n=3); Active compound 50

To 17.2 g of 4-sulfamoylanilide in 8 ml of acetic acid, 12.3 ml of 4-chloro-butyryl chloride were added dropwise at room temperature and under stirring. After two hours, the homogenous paste thus obtained was treated with 33 g of sodium acetate dissolved in 150 ml of water. The entire reaction mass was maintained at room temperature for 12 hours. The solid form was then collected by filtration, washed with water, dried and crystallized from ethanol. Yield 10 g, mp 178°–178.5° C. This intermediate, i.e., 4-sulfamoyl-ω-chlorobutyrylanilide has not to date been described in the literature. To 2.76 g of 4-sulfamoyl-ω-chlorobutyrylanilide, obtained as above, dissolved in 1.5 ml of acetone, 1.06 g of sodium bicarbonate and 1.92 g of 4-(2-pyridyl)-piperazine dissolved in 10 ml of acetone were added. The mixture was refluxed for 16 hours. Upon completion of the reaction, the solid formed was collected by filtration, washed with chloroform, treated with hot 95% ethanol to remove the inorganic salt and then filtered. From concentrated mother liquors there crystallized a product which was collected by filtration and recrystallized from 95% ethanol. Yield 1.08 g of the active compound 50; mp 217°–219° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. An ω-[4-(2-pyridyl)-piperazino]-alkanoylanilide compound having the structural formula (I):

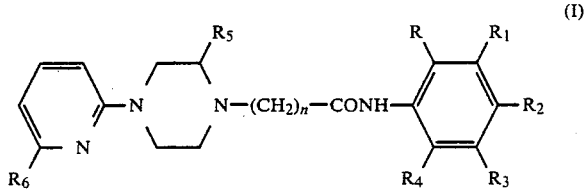

wherein n is 2, a maximum of one of the substituents R, $R_1$, $R_2$, $R_3$ or $R_4$ is halogen, $C_2$ alkoxy, hydroxy, nitro, amino, $C_1$ alkylthio, 1-hydroxy ($C_2$) alkyl, $C_2$ alkanoyl, $C_2$ alkoxycarbonyl, 3-($C_1$) alkylureido or $C_2$ alkoxyoxalylamido, or alternatively two or four of the substituents R, $R_1$, $R_2$, $R_3$ or $R_4$ is a $C_1$ alkyl, the substituents R, $R_1$, $R_2$, $R_3$ and $R_4$ which are not selected from the group identified above are all hydrogen, $R_5$ is hydrogen or $C_1$–$C_4$ alkyl, and $R_6$ is hydrogen or $C_1$–$C_4$ alkoxy, or a pharmaceutically acceptable salt thereof.

2. The anilide compound as defined by claim 1, the same being 3-Nitro-β-[4-(2-pyridyl)-piperazino]-propionanilide.

3. The anilide compound as defined by claim 1, the same being 4-Nitro-β-[4-(2-pyridyl)-piperazino]-propionanilide.

4. The anilide compound as defined by claim 1, the same being 4-Amino-β-[4-(2-pyridyl)-piperazino]-propionanilide.

5. The anilide compound as defined by claim 1, the same being 4-Ethoxyoxalylamido-β-[4-(2-pyridyl)-piperazino]-propionalide.

6. The anilide compound as defined by claim 1, the same being 4-Acetyl-β-[4-(2-pyridyl)-piperazino]-propionanilide.

7. The anilide compound as defined by claim 1, the same being 4-(1-Hydroxyethyl)-β-[4-(2-pyridyl)-piperazino]-propionanilide.

8. The anilide compound as defined by claim 1, the same being 2,3,5,6-Tetramethyl-β-[4-(2-pyridyl)-piperazino]-propionanilide.

9. The anilide compound as defined by claim 1, the same being β-[4-(2-pyridyl)-piperazino]-propionanilide.

10. The anilide compound as defined by claim 1, the same being 2,6-Dimethyl-β-[4-(2-pyridyl)-piperazino]-propionanilide.

11. The anilide compound as defined by claim 1, the same being 4-Ethoxy-β-[4-(2-pyridyl)-piperazino]-propionanilide.

12. The anilide compound as defined by claim 1, the same being 4-Hydroxy-β-[4-(2-pyridyl)-piperazino]-propionanilide.

13. The anilide compound as defined by claim 1, the same being 4-Amino-β-[4-(6-methoxy-2-pyridyl)-piperzino]-propionanilide.

14. The anilide compound as defined by claim 1, the same being 4-(3-Methylureido)-β-[4-(2-pyridyl)-piperazino]-propionanilide.

15. The anilide compound as defined by claim 1, the same being 2-Chloro-β-[4-(2-pyridyl)-piperazino]-propionanilide.

16. The anilide compound as defined by claim 1, the same being 2-Amino-β-[4-(6-methoxy-2-pyridyl)-piperazino]-propionanilide.

17. The anilide compound as defined by claim 1, the same being 3-Acetyl-β-[4-(2-pyridyl)-piperazino]-propionanilide.

18. The anilide compound as defined by claim 1, the same being 4-Ethoxycarbonyl-β-[4-(2-pyridyl)-piperazino]-propionanilide.

19. The anilide compound as defined by claim 1, the same being 4-Methylthio-β-[4-(2-pyridyl)-piperazino]-propionanilide.

* * * * *